(12) United States Patent
Wakita et al.

(10) Patent No.: US 9,288,977 B2
(45) Date of Patent: Mar. 22, 2016

(54) DISINFECTANT DETERGENT COMPOSITION

(75) Inventors: Kazuaki Wakita, Kawasaki (JP); Satoko Matani, Kawasaki (JP)

(73) Assignee: NOF CORPORATION, Tokyo (JP)

( * ) Notice: Subject to any disclaimer, the term of this patent is extended or adjusted under 35 U.S.C. 154(b) by 208 days.

(21) Appl. No.: 13/822,738

(22) PCT Filed: Sep. 12, 2011

(86) PCT No.: PCT/JP2011/005123
§ 371 (c)(1),
(2), (4) Date: Mar. 13, 2013

(87) PCT Pub. No.: WO2012/035751
PCT Pub. Date: Mar. 22, 2012

(65) Prior Publication Data
US 2013/0165528 A1    Jun. 27, 2013

(30) Foreign Application Priority Data

Sep. 14, 2010 (JP) .................................. 2010-205989
Jun. 13, 2011 (JP) .................................. 2011-130828

(51) Int. Cl.
*A01N 25/30* (2006.01)
*A01N 37/12* (2006.01)
*A01N 43/08* (2006.01)
*C11D 1/825* (2006.01)
*C11D 3/48* (2006.01)
*C11D 1/66* (2006.01)
*C11D 1/72* (2006.01)

(52) U.S. Cl.
CPC ................. *A01N 25/30* (2013.01); *A01N 37/12* (2013.01); *A01N 43/08* (2013.01); *C11D 1/825* (2013.01); *C11D 3/48* (2013.01); *C11D 1/667* (2013.01); *C11D 1/72* (2013.01)

(58) Field of Classification Search
CPC ....... A01N 25/30; A01N 43/08; A01N 37/12; A01N 2300/00; A01N 31/02; C11D 1/825; C11D 3/48; C11D 1/72; C11D 1/667

USPC ................................................... 514/724, 777
See application file for complete search history.

(56) References Cited

U.S. PATENT DOCUMENTS 6,596,763 B1 * 7/2003 Thormar et al. .............. 514/506

FOREIGN PATENT DOCUMENTS

| EP | 0512328 | 11/1992 |
|---|---|---|
| JP | 5-140589 | 6/1993 |
| JP | 05-201853 | 8/1993 |
| JP | 2006-124627 | 5/2006 |
| JP | 2006-143777 | 6/2006 |
| JP | 2009-173768 | 8/2009 |
| JP | 2010-037512 | 2/2010 |

OTHER PUBLICATIONS

International Search Report dated Nov. 8, 2011 filed in PCT/JP2011/005123.

* cited by examiner

Primary Examiner — Sarah Pihonak
Assistant Examiner — Jason A Deck
(74) Attorney, Agent, or Firm — Rankin, Hill & Clark LLP

(57) ABSTRACT

A disinfectant detergent composition containing a food or food additive as a main component is provided. The disinfectant detergent composition contains the following components (a), (b), and (c). The sum [a+b] of the component (a) content and the component (b) content of the composition ranges from 0.1% to 30% by mass, the mass ratio [a/b] of the component (a) to the component (b) ranges from 1/2 to 4/1, and the component (c) content of the composition ranges from 60% to 99.5% by mass. (a) polyoxyethylene sorbitan monolaurate (b) a fatty acid glyceride in which the number of carbon atoms of its acyl group ranges from 8 to 12, the monoglyceride content of the component (b) being 85% by mass or more, the mass fraction of 1-monoglyceride relative to the total amount of monoglycerides being in the range of 0.9 to 1.0 (c) water and/or ethanol.

1 Claim, No Drawings

DISINFECTANT DETERGENT COMPOSITION

TECHNICAL FIELD

The present invention relates to a disinfectant detergent composition and more particularly to a disinfectant detergent composition that contains a food or a food additive as a main component.

BACKGROUND ART

With the growing safety awareness of consumers, there is increasing demand for safer detergents. In particular, infants may accidentally swallow a detergent or lick a surfactant remaining on fingers. Thus, there is a demand for detergents containing a food additive surfactant, which is safe even in the case of accidental ingestion and has disinfection and cleaning effects.

"Guidelines for Measures against Novel Influenza (Feb. 17, 2009)" drawn up by the Ministry of Health, Labour and Welfare of Japan in response to a recent pandemic of novel influenza suggests the importance of "hand-washing" as an effective infection preventive measure. A hand-washing method generally involves washing hands, for example, with soap suds. It is desirable to use safe detergent components in such hand soaps for infants and children.

For example, polyglycerin fatty acid ester and sucrose fatty acid ester surfactants are food additives, but these surfactants have poor foaming characteristics, and use of such surfactants as detergent components may result in insufficient hand-washing. Thus, there is a demand for detergents that contain a food additive surfactant as a main component and have satisfactory foaming characteristics. Another infection preventive measure other than hand-washing may be a method for spraying and rubbing hands with an antiseptic solution, such as an alcohol preparation. Recently, for infants, who cannot rub their hands evenly with sprayed antiseptic solution, an antiseptic foam that can entirely cover their hands for disinfection has been commercially available. However, use of such a food additive surfactant as a detergent component may result in not only poor foaming but also precipitation during cold storage because of poor compatibility of a polyglycerin fatty acid ester or a sucrose fatty acid ester with an alcohol. Thus, there is a demand for an antiseptic foam that can entirely cover hands with abundant foam even in the presence of a large amount of alcohol and has good low-temperature stability.

Polyoxyethylene sorbitan fatty acid esters are surfactants that were designated as food additives in Japan in April, 2008. Polyoxyethylene sorbitan fatty acid esters are less irritating to the human body and are compatible with solvents, such as water and alcohols. Thus, attempts are being made to use polyoxyethylene sorbitan fatty acid esters in applications that require a high degree of safety, such as washing of vegetables and infant feeding bottles, as well as food applications.

Detergents that contain polyoxyethylene sorbitan fatty acid esters are described in Patent Literatures 1 and 2, for example. Patent Literature 1 proposes a disinfectant detergent composition for toilet seats containing one or more nonionic surfactants. The disinfectant detergent composition contains (A) a lower alcohol, (B) an organic acid and an alkali metal salt thereof, or an inorganic acid and an alkali metal salt thereof, and (C) a polyoxyethylene sorbitan fatty acid ester. This detergent composition has improved low-temperature storage stability and excellent disinfection effects but does not have satisfactory foaming characteristics.

Patent Literature 2 proposes a detergent for food that contains (A) a polyoxyethylene sorbitan fatty acid monoester and (B) a lipophilic polyhydric alcohol fatty acid monoester having HLB of 8 or less. This detergent for food washes well but does not have satisfactory foaming characteristics.

Furthermore, the lipophilic polyhydric alcohol fatty acid monoester may be precipitated during cold storage, resulting in low storage stability.

Thus, no disinfectant detergent is available that contains a food or a food additive as a main detergent component and has satisfactory foaming characteristics, excellent disinfection effects, and excellent low-temperature stability.

CITATION LIST

Patent Literature

PTL 1: Japanese Unexamined Patent Application Publication No. 2009-173768
PTL 2: Japanese Unexamined Patent Application Publication No. 2010-37512

SUMMARY OF INVENTION

Technical Problem

In order to solve these problems, it is an object of the present invention to provide a disinfectant detergent that contains a food or a food additive as a main detergent component and has satisfactory foaming characteristics, excellent disinfection effects, and excellent low-temperature stability.

Solution to Problem

As a result of extensive studies to solve the problems described above, the present inventor found a disinfectant detergent that has the features of the present invention and thereby has satisfactory foaming characteristics, excellent disinfection effects, and excellent low-temperature stability.

The present invention relates to a disinfectant detergent composition that contains the following components (a), (b), and (c), wherein the sum [a+b] of the component (a) content and the component (b) content of the composition is in the range of 0.1% to 30% by mass, the mass ratio [a/b] of the component (a) to the component (b) is in the range of 1/2 to 4/1, and the component (c) content of the composition is in the range of 60% to 99.5% by mass.

(a) polyoxyethylene sorbitan monolaurate
(b) a fatty acid glyceride in which the number of carbon atoms of its acyl group is in the range of 8 to 12, the monoglyceride content of the component (b) being 85% by mass or more, the mass fraction of 1-monoglyceride relative to the total amount of monoglycerides being in the range of 0.9 to 1.0
(c) water and/or ethanol

Advantageous Effects of Invention

A disinfectant detergent composition according to the present invention contains a polyoxyethylene sorbitan monolaurate that is a food or a food additive as a main surfactant component. Thus, the disinfectant detergent composition is less irritating and safe and is particularly suitable for hand-washing as well as washing and disinfection of foods, dishes, and infant feeding bottles. In a disinfectant detergent composition according to the present invention, the blend ratio of the polyoxyethylene sorbitan monolaurate to the fatty acid monoglyceride is in a particular range. Thus, the disinfectant detergent composition has excellent foaming characteristics, low-temperature stability, and disinfection effects. A composition containing the components (a) to (c) according to the present invention has disinfection effects for a long time. Thus, the composition can be resistant to the contamination of microorganisms without the addition of a preservative agent.

DESCRIPTION OF EMBODIMENTS

The present invention will be described in detail below.

The component (a), a polyoxyethylene sorbitan monolaurate, is an ethylene oxide adduct of a sorbitan fatty acid ester, which is a partial ester of sorbitol or sorbitan and lauric acid, and is a nonionic surfactant.

The polyoxyethylene sorbitan fatty acid ester may have any structure and has a Griffin HLB in the range of 14 to 19, preferably 15 to 18, more preferably 16 to 17. When the polyoxyethylene sorbitan fatty acid ester has HLB of less than 14, the detergent sometimes does not have satisfactory foaming characteristics. When the polyoxyethylene sorbitan fatty acid ester has HLB of more than 19, the detergent may have no appreciable disinfection effects.

The fatty acid residue of the component (a) is lauric acid. When the fatty acid has less than 12 carbon atoms, the detergent is not likely to have satisfactory foaming characteristics. When the fatty acid has more than 12 carbon atoms, this tends to result in a slight deterioration in foaming characteristics and insufficient disinfection effects. Mixed fatty acids may be used, provided that the ratio of lauric acid to the total amount of fatty acids is 50% by mass or more. Fatty acids mainly composed of lauric acid derived from natural fats and oils, such as coconut oil and palm kernel oil, may also be used.

The component (b) of the present invention is a fatty acid glyceride in which the number of carbon atoms of its acyl group is in the range of 8 to 12, the monoglyceride content of the component (b) being 85% by mass or more, the mass fraction of 1-monoglyceride relative to the total amount of monoglycerides being in the range of 0.9 to 1.0.

The fatty acid glyceride can be produced by an esterification reaction between a fatty acid and glycerin or a transesterification reaction between a fat or an oil and a fatty acid ester and glycerin. A glyceride produced by a reaction is referred to as a reaction glyceride.

In general, a reaction glyceride is a mixture containing 1-monoglyceride as a main component and 2-monoglyceride, 1,3-diglyceride, 1,2-diglyceride, triglyceride, and glycerin as accessory components. The monoglyceride purity of a reaction glyceride can be increased by distillation. A monoglyceride obtained by distillation is referred to as a distilled monoglyceride.

In the present invention, the monoglyceride content of the component (b) is 85% by mass or more, preferably 88% by mass or more, more preferably 92% by mass or more. When the monoglyceride content of the component (b) is less than 85% by mass, this results in unsatisfactory foaming characteristics, low-temperature stability, and disinfection effects.

The monoglyceride content can be measured by gas chromatography in accordance with routine procedures after a sample is subjected to silyl etherification as a pretreatment.

The mass fraction of 1-monoglyceride relative to the total amount of monoglycerides in the component (b) is in the range of 0.9 to 1.0, preferably 0.92 to 1.0, more preferably 0.94 to 1.0. Monoglycerides are classified into two structural isomers: 1-monoglyceride and 2-monoglyceride. The mass fraction of 1-monoglyceride relative to the total amount of monoglycerides is the mass fraction of 1-monoglyceride relative to the total mass of 1-monoglyceride and 2-monoglyceride.

The hydroxy groups of 2-monoglyceride are separated from each other at both ends (positions 1 and 3) of glycerol. In contrast, the hydroxy groups of 1-monoglyceride are localized (positions 2 and 3) and increase the hydrophilicity of the molecule. This can be confirmed by the fact that the spot of 1-monoglyceride is disposed below the spot of 2-monoglyceride (higher hydrophilicity and higher interaction with silica) in thin-layer chromatography using a silica plate.

In the present invention, use of the component (b) in which the mass fraction of 1-monoglyceride relative to the total amount of monoglycerides is in the range of 0.9 to 1.0 is essential to have satisfactory foaming characteristics and disinfection effects. When the mass fraction of 1-monoglyceride is less than 0.9, this results in unsatisfactory foaming characteristics and disinfection effects.

The mass fraction of 1-monoglyceride relative to the total amount of monoglycerides can be calculated using the following equation from the abundance ratio of a proton attached to a carbon atom at position 2 of glycerol (*1 and *2 in the following formulae (1) and (2)) measured by $^1$H-NMR.

[Mass fraction of 1-monoglyceride relative to the total amount of monoglycerides] = [Math. 1]

$$\frac{[\text{Peak area of hydrogen atom *1 in Chemical formula (1)}]}{([\text{Peak area of hydrogen atom *1 in Chemical formula (1)}] + [\text{Peak area of hydrogen atom *2 in Chemical formula (2)}])}$$

A hydrogen atom *1 of 1-monoglyceride is observed at 3.9 ppm, and a hydrogen atom *2 of 2-monoglyceride is observed at 4.9 ppm.

[Chem. 1]

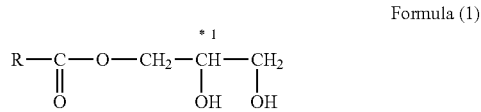

Formula (1)

[Chem. 2]

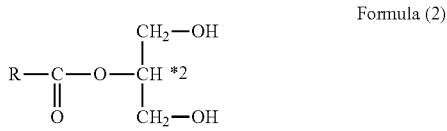

Formula (2)

In the present invention, the number of carbon atoms of the acyl group of the component (b) is in the range of 8 to 12, more preferably 8 to 10, still more preferably 8. The purity of a fatty acid having 8 to 12 carbon atoms serving as a raw material is preferably 88% by mass or more, more preferably 90% by mass or more, still more preferably 92% by mass or more. For example, when a fatty acid having more than 12 carbon atoms is a main component, the disinfectant detergent has not only poor low-temperature stability but also unsatisfactory foaming characteristics and disinfection effects. When a fatty acid having less than 8 carbon atoms is a main component, the disinfectant detergent has unsatisfactory foaming characteristics.

The component (b) may contain a reaction monoglyceride or a distilled monoglyceride prepared by any method or a commercial monoglyceride, provided that the monoglyceride conditions satisfy the requirements of the present invention.

The component (c) in the present invention is water and/or ethanol. The water is preferably purified water, such as distilled water or ion-exchanged water. The ethanol may be manufactured by alcoholic fermentation or an organic synthesis method. Water and ethanol may be used alone or in combination.

In the present invention, the sum [a+b] of the component (a) content and the component (b) content of the composition is in the range of 0.1% to 30% by mass, preferably 0.3% to 25% by mass, more preferably 0.5% to 20% by mass. A sum [a+b] of more than 30% by mass results in unfavorably high costs because of an excessively high surfactant content and also results in dry skin in some users because of excessively high degreasing power of the detergent. A sum [a+b] of less than 0.1% by mass results in unsatisfactory foaming characteristics and disinfection effects. In the present invention, the mass ratio [a/b] of the component (a) to the component (b) is in the range of 1/2 to 4/1, preferably 2/3 to 3.5/1, more preferably 1/1 to 3/1.

A mass ratio [a/b] of more than 4/1 results in unsatisfactory foaming characteristics and disinfection effects. A mass ratio [a/b] of less than 1/2 results in unsatisfactory foaming characteristics and low-temperature stability.

In the present invention, the component (c) content of the composition is in the range of 60% to 99.5% by mass, preferably 70% to 99.0% by mass, more preferably 80% to 98.5% by mass.

When the component (c) is a mixed solvent of water and ethanol, the ratio of water to ethanol is not particularly limited and may be determined for each detergent. For example, for hand soap, water may be the main solvent, and ethanol may constitute up to 30% by mass of the total amount of solvent. For disinfectant detergent foam, ethanol preferably constitutes 30% to 85% by mass, more preferably 40% to 80% by mass, of the total amount of solvent.

In the present invention, although the disinfectant detergent composition may have any pH, the pH of its stock solution is preferably in the range of 5.0 to 8.0, more preferably 5.5 to 7.8, still more preferably 6.0 to 7.5, at 25° C. When the pH of the disinfectant detergent composition deviates considerably from neutral, the component (a) or the component (b) may be hydrolyzed.

A polysaccharide or a derivative thereof designated as a food or a food additive may be used to modify the viscosity or the foam property of a detergent composition according to the present invention. Examples of the polysaccharide or the derivative thereof include gum arabic, alginic acid and salts thereof, propylene glycol alginate and salts thereof, carrageenan, gum ghatti, curdlan, xanthan gum, guar gum, chitosan, gellan gum, hydroxypropylcellulose, hydroxypropylmethylcellulose, carboxymethylcellulose and salts thereof, tamarind seed gum, tara gum, pullulan, and pectin. Among these, comprehensively considering the basic functions of a detergent, such as transparent solubility in water, storage stability at different temperatures, effects of improving foam property, thickening effects, and rinsing, preferred examples include alginic acid and salts thereof, propylene glycol alginate and salts thereof, hydroxypropylcellulose, hydroxypropylmethylcellulose, and carboxymethylcellulose and salts thereof, and more preferred examples include alginic acid and salts thereof, hydroxypropylmethylcellulose, and carboxymethylcellulose and salts thereof.

Another component may be added to a detergent composition according to the present invention without losing the advantages of the present invention. Examples of the additive component include surfactants other than the surfactants specified in the present invention, such as polyglycerin fatty acid esters and sucrose fatty acid esters; fats and oils, such as vegetable oils and fats, animal oils and fats; hydrocarbon oils, such as squalene and liquid paraffin; solvents, such as propylene glycol and glycerin; builders, such as citric acid and salts thereof, succinic acid and salts thereof, malic acid and salts thereof, tartaric acid and salts thereof, ethylenediaminetetraacetic acid and salts thereof, and metaphosphoric acid and salts thereof; antioxidants, such as tocopherols; polysaccharides; amino acids; peptides; and preservatives, perfumes, and colorants other than the components of a composition of the present invention.

Since the present invention includes a disinfectant detergent composition that contains a food or a food additive as a main component, the present invention is suitably for detergents that are safe even in the case of accidental ingestion, such as detergents for vegetables, detergents for infant feeding bottles, and kitchen detergents, as well as hand soaps and antiseptic foams.

A detergent composition according to the present invention has disinfection effects for a long time. Thus, the composition can be resistant to the contamination of microorganisms without the addition of a preservative agent. Thus, the present invention also functions as a preservative composition. Furthermore, the components (a) to (c) in the present invention can be added to any formulations, for example, skin care preparations, such as lotions, milky lotions, creams, liquid foundations, facial cleansers, and cleansing creams, and haircare products, such as hair shampoos, hair conditioners, hair treatments, and hair styling products, as well as the applications described above, such that the components (a) to (c) satisfy the quantitative relations defined in the present invention, thereby imparting antiseptic effects to the formulations. Thus, the present invention can also provide a method for imparting antiseptic effects to various formulations.

EXAMPLES

Although the present invention will be described in more detail in the following examples, the present invention is not limited to these examples. Unless otherwise specified, "%" in the following description denotes "% by mass".

Hand soaps having formulations shown in Tables 2 and 3 and antiseptic foams having formulations shown in Table 4 were prepared. The 1) foaming characteristics, the 2) low-temperature stability, and the 3) disinfection effects of these detergents were evaluated. Tables 2 to 4 show the results.

In Tables 2 to 4, a "component (a)" and a "component (b)" denote the component (a) and the component (b) according to the present invention, and a "component (a')" and a "component (b')" denote comparative components of the component (a) and the component (b). The "component (b)" and the "component (b')" are commercial products and have fatty acid residues, the monoglyceride content, and the mass fraction of 1-monoglyceride shown in the following Table 1.

[Table 1]

TABLE 1

| Fatty acid glyceride | Monoglyceride content (mass %) | Mass fraction of 1-monoglyceride | Note |
|---|---|---|---|
| Monocaprylic acid monoglyceride (1) | 91.8 | 0.956 | Component b |
| Monolauric acid monoglyceride | 92.2 | 0.934 | |
| Monocaprylic acid monoglyceride (2) | 56.0 | 0.803 | Component b' |
| Monocaprylic acid monoglyceride (3) | 89.6 | 0.872 | |
| Monostearic acid monoglyceride | 85.3 | 0.915 | |

The monoglyceride content was measured by gas chromatography (GC). The GC conditions are as follows:
Column: OV-1 1.1 m
Oven temperature: 130° C. (3 min hold)→340° C. (6 min hold)
Injection and detection temperature: 350° C.
Carrier gas: He 50 mL/min
Heating Rate: 10° C./min
Detector: FID
Pretreatment: silyl etherification The mass fraction of 1-monoglyceride was calculated from a NMR spectrum using the above-mentioned equation.

<Preparation of Disinfectant Detergent Composition>

Hand Soap

Hydroxypropylmethylcellulose, sodium carboxymethylcellulose, or sodium alginate shown in Tables 2 and 3 was dispersed in ion-exchanged water at normal temperature (approximately 25° C.) and, after ensuring that no lumps were formed, was heated to 80° C. in a water bath while stirring. All the components other than ethanol were then charged. Ensuring that the components were dissolved, the solution was cooled to 40° C. or less. Ethanol was added to the solution at 40° C. or less and was stirred until the solution becomes homogeneous, thus yielding a hand soap.

Antiseptic Foam

Ion-exchanged water and ethanol shown in Table 4 were charged at normal temperature (approximately 25° C.) and were homogeneously dissolved. The other raw materials were then charged. The other raw materials were homogeneously dissolved at normal temperature while stirring to yield an antiseptic foam.

<Evaluation of Hand Soap>

Foaming Characteristics

A 5% by mass aqueous solution of a hand soap was stirred with a Millser testing machine (IFM-100, manufactured by Iwatani) for 5 seconds. After leaving the solution still for 1 minute, the height of foam was measured. Rating was based on the following criteria, wherein AA and A were acceptable.
Rating: Criterion
AA: The height of foam was 30 mm or more.
A: The height of foam was 25 mm or more and less than 30 mm.
B: The height of foam was 20 mm or more and less than 25 mm.
C: The height of foam was less than 20 mm.

Low-Temperature Stability

A 50-mL screw tube was filled with 50 g of a hand soap prepared as described above, was hermetically sealed, and was stored in a thermostat at 5° C. for 1 month. After the test, the properties of the sample were evaluated in accordance with the following criteria.

Circle: The sample had no change in appearance.
Cross: The sample had a change in appearance, such as precipitation or solidification.

Disinfection Effects

Evaluation was performed by a sanitizer test method according to the Association of Official Agricultural Chemists (AOAC). More specifically, 0.1 mL of a bacterial suspension was added to 9.9 mL of a stock solution of a test agent. The bacterial suspension contained $10^8$ to $10^9$ bacteria in a Nutrient Broth (NB) culture medium (manufactured by Merck & Co., Inc.). After contact for 30 seconds, 1 mL of the stock solution was added to 9 mL of a phosphate buffer containing a deactivator and was immediately subjected to serial dilution. The stock solution was mixed with a plate count agar (PCA) culture medium (manufactured by Merck & Co., Inc.) and was cultured at 37° C. for 48 hours. After 7 days, the number of living bacteria was counted. A log reduction was calculated from a logarithmic difference between the number of seeded bacteria and the number of living bacteria and was rated in accordance with the following criteria. The test bacteria were *Escherichia coli* (*Escherichia coli* IFO-12734) and *Staphylococcus aureus* (*Staphylococcus aureus* IFO-12732).

A sample was judged to be acceptable when the number of living bacteria after culture for 7 days was below the detection limit and when the log reduction after culture for 48 hours was rated AA or A in accordance with the following criteria.
Rating: Criterion
AA: The log reduction of the test bacterium was 5 or more.
A: The log reduction of the test bacterium was 4 or more and less than 5.
B: The log reduction of the test bacterium was 3 or more and less than 4.
C: The log reduction of the test bacterium was less than 3.
When the ratings of the log reductions of the two test bacteria were different, a lower rating was employed.
Even when the rating of the log reduction after culture for 48 hours was AA or A, observation of living bacteria after culture for 7 days was judged to be unsatisfactory (rating: C).

<Evaluation of Antiseptic Foam>

Foaming Characteristics

An antiseptic foam was charged into a 100-mL foamer container (ejection rate: 0.8±0.5 g) and was discharged into a 300-mL graduated cylinder by pressing the foamer container 10 times. After leaving the graduated cylinder still for 1 minute, the volume of foam was measured. Rating was based on the following criteria, wherein AA and A were acceptable.
Rating: Criterion
AA: The volume of foam was 90 mL or more.
A: The volume of foam was 80 mL or more and less than 90 mL.
B: The volume of foam was 60 mL or more and less than 80 mL.
C: The volume of foam was less than 60 mm.

Low-Temperature Stability

A 50-mL screw tube was filled with 40 g of an antiseptic foam prepared as described above, was hermetically sealed, and was stored in a thermostat at 5° C. for 1 month. After the test, the properties of the sample were evaluated in accordance with the following criteria.
Circle: The sample had no change in appearance.
Cross: The sample had a change in appearance, such as precipitation.

Disinfection Effects

Evaluation was performed by a sanitizer test method according to the Association of Official Agricultural Chemists (AOAC).

TABLE 2

Hand Soap

| | | Example | | | | | | |
|---|---|---|---|---|---|---|---|---|
| | | 1 | 2 | 3 | 4 | 5 | 6 | 7 |
| Component a | Monolauric acid POE*[1](20) sorbitan | 15.0 | 6.0 | 4.0 | 7.0 | 4.8 | 5.0 | 6.0 |
| Component b | Monocaprylic acid monoglyceride (1) | 4.0 | 4.0 | 4.0 | | 3.2 | 1.0 | 4.0 |
| | Monolauric acid monoglyceride | 1.0 | | | 3.0 | | 3.0 | |
| Component c | Ethanol | 4.0 | | 2.0 | 6.0 | | | 4.0 |
| | Ion-exchanged water | | | | Balance | | | |
| Other components | Hydroxypropylmethylcellulose | 0.8 | 0.8 | 0.8 | 0.8 | | | 0.2 |
| | Sodium carboxymethylcellulose | | | | | 0.6 | | 0.2 |
| | Sodium alginate | | | | | | 0.6 | 0.2 |
| | Glycerin | 4.0 | 4.0 | 4.0 | 4.0 | | | |
| | Propylene glycol | | | | | 8.0 | 8.0 | 4.0 |
| | Disodium ethylenediaminetetraacetate | | | | | 0.2 | 0.2 | 0.2 |
| | Citric acid | 0.05 | 0.05 | 0.05 | 0.05 | | | |
| | Sodium citrate | 0.45 | 0.45 | 0.45 | 0.45 | 0.40 | 0.40 | 0.50 |
| Total | | | | | 100 | | | |
| pH (5% aq) | | 6.4 | 6.4 | 6.5 | 6.4 | 6.2 | 6.3 | 6.8 |
| Rating | Foaming characteristics | A | AA | A | A | AA | A | A |
| | Low-temperature stability | ○ | ○ | ○ | ○ | ○ | ○ | ○ |
| | Disinfection effect | AA | A | A | A | A | A | AA |

*[1]POE = Polyoxyethylene

TABLE 3

Hand soap

| | | Comparative example | | | | | | | | | |
|---|---|---|---|---|---|---|---|---|---|---|---|
| | | 1 | 2 | 3 | 4 | 5 | 6 | 7 | 8 | 9 | 10 |
| Component a | Monolauric acid POE*[1](20) sorbitan | 9.0 | 1.0 | 0.03 | | | | 6.0 | 6.0 | 6.0 | 6.0 |
| Component a' | Monooleic acid POE*[1](20) sorbitan | | | | 6.0 | | | | | | |
| | Decaglycerin monolaurate | | | | | 6.0 | | | | | |
| | Sucrose monolauric acid ester | | | | | | 6.0 | | | | |
| Component b | Monocaprylic acid monoglyceride (1) | 1.0 | 9.0 | 0.02 | 4.0 | 4.0 | 4.0 | | | | |
| | Monolauric acid monoglyceride | | | | | | | | | | |
| Component b' | Monocaprylic acid monoglyceride (2) | | | | | | | 4.0 | | | |
| | Monocaprylic acid monoglyceride (3) | | | | | | | | 4.0 | | |
| | Monostearic acid monoglyceride | | | | | | | | | 4.0 | |
| | Monocaprylic acid propylene glycol | | | | | | | | | | 4.0 |
| Component c | Ethanol | | | 10.0 | 10.0 | | | | | | |
| | Ion-exchanged water | | | | Balance | | | | | | |
| Other components | Hydroxypropylmethylcellulose | | | | 0.8 | | | | | | |
| | Glycerin | | | | 4.0 | | | | | | |
| | Citric acid | | | | 0.05 | | | | | | |
| | Sodium citrate | | | | 0.45 | | | | | | |
| Total | | | | | 100 | | | | | | |
| pH (5% aq) | | 6.3 | 6.4 | 6.3 | 6.4 | 6.4 | 6.5 | 6.4 | 6.5 | 6.4 | 6.2 |
| Rating | Foaming characteristics | C | C | C | C | B | B | C | B | C | C |
| | Low-temperature stability | ○ | x | ○ | ○ | x | x | x | ○ | x | x |
| | Disinfection effect | C | A | C | C | B | C | C | B | C | C |

*[1]POE = Polyoxyethylene

TABLE 4

Antiseptic foam

| | | Example | | | Comparative example | | | | | | | |
|---|---|---|---|---|---|---|---|---|---|---|---|---|
| | | 8 | 9 | 10 | 11 | 12 | 13 | 14 | 15 | 16 | 17 | 18 |
| Component a | Monolauric acid POE*[1](20) sorbitan | 1.2 | 2.0 | 0.6 | | | 2.0 | | | 1.2 | 1.2 | 1.2 |

TABLE 4-continued

| | | Antiseptic foam | | | | | | | | | | |
|---|---|---|---|---|---|---|---|---|---|---|---|---|
| | | Example | | | Comparative example | | | | | | | |
| | | 8 | 9 | 10 | 11 | 12 | 13 | 14 | 15 | 16 | 17 | 18 |
| Component a' | Monooleic acid POE*[1](20) sorbitan | | | | | | | 1.2 | | | | |
| | Sucrose monolauric acid ester | | | | | | | | 1.2 | | | |
| Component b | Monocaprylic acid monoglyceride (1) | 0.8 | 2.0 | 0.3 | | 2.0 | | 0.8 | 0.8 | | | |
| Component b' | Monocaprylic acid monoglyceride (2) | | | | | | | | | 0.8 | | |
| | Monocaprylic acid monoglyceride (3) | | | | | | | | | | 0.8 | |
| | Monocaprylic acid propylene glycol | | | | | | | | | | | 0.8 |
| Component c | Ethanol | 58.0 | 75.0 | 35.0 | 58.0 | 58.0 | 58.0 | 58.0 | 58.0 | 58.0 | 58.0 | 58.0 |
| | Ion-exchanged water | | Balance | | | | | Balance | | | | |
| | Lactic acid | | 0.10 | | | | | 0.10 | | | | |
| | Sodium lactate | | 0.40 | | | | | 0.40 | | | | |
| Total | | | 100 | | | | | 100 | | | | |
| pH (5% aq) | | 7.2 | 7.3 | 7.1 | 7.1 | 7.2 | 7.0 | 7.2 | 7.2 | 7.3 | 7.2 | 7.2 |
| Rating | Foaming characteristics | AA | A | A | C | C | B | B | A | C | B | C |
| | Low-temperature stability | ○ | ○ | ○ | ○ | × | ○ | ○ | × | × | ○ | ○ |
| | Disinfection effect | AA | AA | A | C | A | B | B | B | B | B | C |

*[1]POE = Polyoxyethylene

The results in Tables 2 to 4 show that all the detergent compositions according to the examples of the present invention had satisfactory foaming characteristics, low-temperature stability, disinfection effects, and antiseptic effects.

In contrast, among the comparative examples in Table 3, Comparative Example 1, which had [a/b] of more than 4/1, had poor foaming characteristics, disinfection effects, and antiseptic effects, and Comparative Example 2, which had a/b of less than 1/2, had poor foaming characteristics and low-temperature stability. Comparative Example 3, which had [a+b] of less than 0.1, had poor foaming characteristics, disinfection effects, and antiseptic effects. Comparative Examples 4 to 6 did not contain the component (a) but instead contained the sorbitan fatty acid ester, the polyglycerol fatty acid monoester, or the sucrose fatty acid monoester, each having a fatty acid containing a different number of carbon atoms from the component (a). Thus, Comparative Examples 4 to 6 had poor foaming characteristics, low-temperature stability, disinfection effects, or antiseptic effects. Comparative Examples 7 to 10 did not contain the component (b), had the monoglyceride content, the mass fraction of 1-monoglyceride, or the number of carbon atoms of a fatty acid outside the scope of the present invention, and contained a non-glyceride instead. Thus, Comparative Examples 7 to 10 had poor foaming characteristics, low-temperature stability, disinfection effects, or antiseptic effects.

Comparative Examples 11 to 18 in Table 4 contained neither the component (a) nor the component (b) of the present invention (Comparative Example 11) or no component (a) or no component (b) (Comparative Examples 12 and 13) or contained an alternative of the component (a) or the component (b) (Comparative Examples 14 to 18). Thus, Comparative Examples 11 to 18 had poor foaming characteristics, low-temperature stability, disinfection effects, or antiseptic effects.

The invention claimed is:

1. A disinfectant detergent composition, comprising: the following components (a); (b); and (c), wherein the sum [a+b] of the component (a) content and the component (b) content of the composition is in the range of 0.1% to 30% by mass, the mass ratio [a/b] of the component (a) to the component (b) is in the range of 1/1 to 3/2, and the component (c) content of the composition is in the range of 60% to 99.5% by mass,
   (a) polyoxyethylene sorbitan monolaurate;
   (b) a fatty acid glyceride in which the number of carbon atoms of its acyl group is 8, the monoglyceride content of the component (b) being 85% by mass or more, the mass fraction of 1-monoglyceride relative to the total amount of monoglycerides being in the range of 0.9 to 1.0; and
   (c) water and/or ethanol.

* * * * *